United States Patent [19]

Katz

[11] Patent Number: 5,009,507

[45] Date of Patent: Apr. 23, 1991

[54] METHOD OF EVALUATING MECONIUM CONTENT OF AMNIOTIC FLUID

[76] Inventor: Michael Katz, 3848 California Ave., San Francisco, Calif. 94118

[21] Appl. No.: 496,684

[22] Filed: Mar. 21, 1990

[51] Int. Cl.$^5$ .............................................. G01J 3/52
[52] U.S. Cl. ................................................... 356/421
[58] Field of Search ............... 356/421, 422, 423, 424; 128/665

[56] References Cited

U.S. PATENT DOCUMENTS

| | | | |
|---|---|---|---|
| 2,009,943 | 7/1935 | Munsell et al. | 356/421 |
| 2,027,816 | 1/1936 | Drucker | 356/423 |
| 2,209,764 | 7/1940 | Cassen et al. | 356/412 |
| 4,856,527 | 8/1989 | Karcher et al. | 128/665 |

FOREIGN PATENT DOCUMENTS

| | | | |
|---|---|---|---|
| 2034870 | 1/1972 | Fed. Rep. of Germany | 128/665 |
| 2215658 | 10/1973 | Fed. Rep. of Germany | 128/665 |

*Primary Examiner*—F. L. Evans
*Attorney, Agent, or Firm*—Flehr, Hohbach, Test, Albritton & Herbert

[57] ABSTRACT

A method of evaluating the maconium content or concentration of amniotic fluid makes uses of a meconium measurement color chart which accurately reproduces the color and transparency of amniotic fluid having different amounts of meconium therein. Measurement indicia are denoted on the chart next to corresponding color samples. A sample of amniotic fluid is placed either on a transparent medium or in a transparent container. Then the sample is visually compared with the meconium measurement chart, while shining fluorescent light through both the sample and the meconium measurement chart, so as to determine the denoted measurement value which most closely matches the color and transparency of the amniotic fluid sample. If the measurement value is above a predefined threshold value, precautionary measures are taken to improve the infant's chances of survival, e.g., by intubating the infant's lungs.

6 Claims, 1 Drawing Sheet

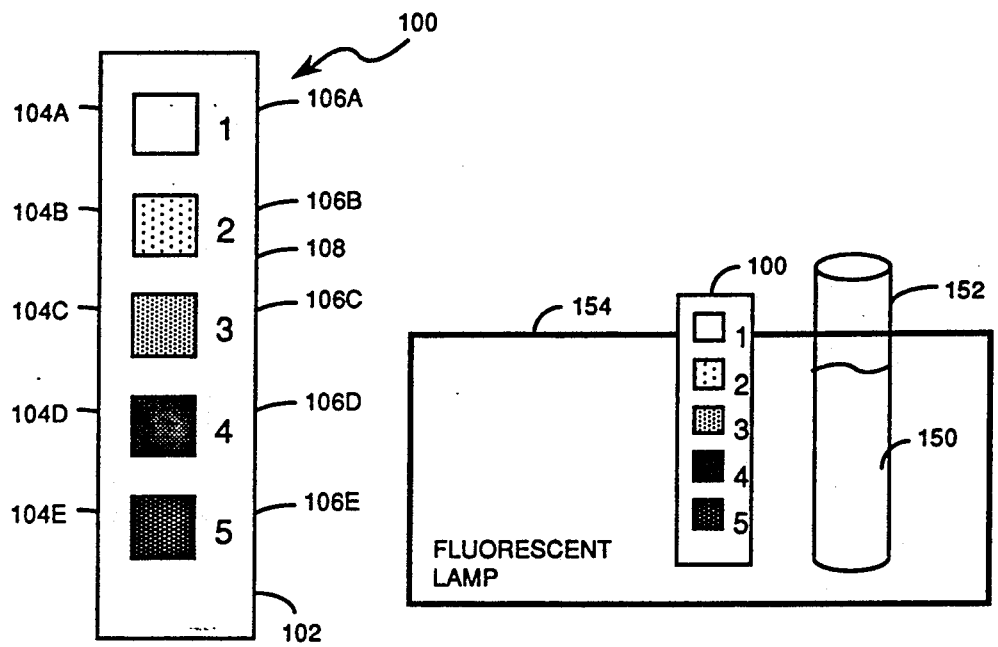
FIGURE 1
FIGURE 3
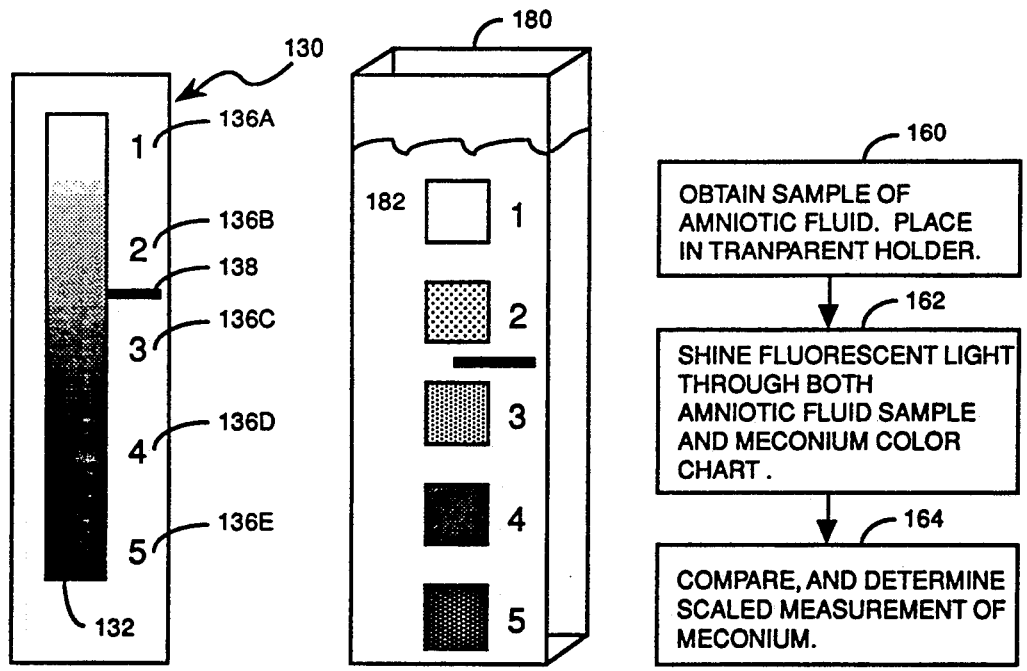
FIGURE 2
FIGURE 5
FIGURE 4

METHOD OF EVALUATING MECONIUM CONTENT OF AMNIOTIC FLUID

The present invention relates generally to systems and methods of evaluating the health of human fetuses, and particularly to methods and systems for evaluating the meconium content of amniotic fluid.

BACKGROUND OF THE INVENTION

Meconium is excrement in the intestinal tract of a fetus. In a large majority of human fetuses, meconium is excreted shortly (e.g., with one or two days) after birth. However, approximately eight to sixteen percent of human fetuses discharge at least some meconium into the mother's amniotic sac prior to birth. Some fraction of those fetuses aspirate meconium into their lungs, and approximately one to two percent of those infants die from complications caused by the aspiration of meconium. Thus, the aspiration of meconium is a life threatening problem for approximately ten to twenty out of every ten thousand babies born.

If it is known that there is a significant amount of meconium in the amniotic fluid, it is possible to undertake measures to improve the baby's chances of survival. In particular, it is possible to intubate the baby's lungs immediately after birth so as to remove amniotic fluid in the baby's wind pipe and thereby remove as much meconium as possible from the baby's wind pipe and lungs.

In the prior art, there have been two primary techniques used to evaluate the meconium content of amniotic fluid. One, has been to use spectrophotometry. This technique requires a laboratory, uses expensive equipment, and is sufficiently expensive and difficult that it is not used routinely.

The second prior art technique is to simply visually inspect the amniotic fluid, often just by looking at the fluid which has been expelled during labor. If the fluid looks clear, the doctor concludes that there is probably little or no meconium present. If the fluid looks "thick" or dark, precautionary measures are taken to intubate the baby's lungs. Unfortunately, amniotic fluid that looks relatively clear upon casual inspection may contain significant amounts of meconium. Nevertheless, this technique is the main one used routinely in the prior art, because it is inexpensive, even though it is insufficiently accurate to provide a reliable indication of meconium content.

The present invention provides a simple method of evaluating meconium content which is both very inexpensive and simple to use.

SUMMARY OF THE INVENTION

In summary, the present invention is a method of evaluating the meconium content or concentration of amniotic fluid. The method makes use of a meconium measurement color chart which accurately reproduces the color and transparency of amniotic fluid having different amounts of meconium therein. Measurement indicia are denoted on the chart next to corresponding color samples. A sample of amniotic fluid is placed either on a transparent medium or in a transparent container. Then the sample is visually compared with the meconium measurement chart, while shining fluorescent light through both the sample and the meconium measurement chart, so as to determine the denoted measurement value which most closely matches the color and transparency of the amniotic fluid sample. If the measurement value is above a predefined threshold value, precautionary measures are taken to improve the infant's chances of survival, e.g., by intubating the infant's lungs.

BRIEF DESCRIPTION OF THE DRAWINGS

Additional objects and features of the invention will be more readily apparent from the following detailed description and appended claims when taken in conjunction with the drawings, in which:

FIG. 1 schematically depicts a first preferred embodiment of a meconium measurement chart for use in evaluating the meconium content of amniotic fluid.

FIG. 2 schematically depicts a second preferred embodiment of a meconium measurement chart for use in evaluating the meconium content of amniotic fluid.

FIG. 3 is a block diagram of apparatus for evaluating the meconium content of an amniotic fluid sample.

FIG. 4 is a flow chart of the process of the present invention for determining the meconium content of an amniotic fluid sample.

FIG. 5 depicts an amniotic fluid container with a meconium measurement chart imprinted thereon for evaluating the meconium content of an amniotic fluid sample.

DESCRIPTION OF THE PREFERRED EMBODIMENTS

It is well known that the amount of amniotic fluid in the amniotic sac varies from fetus to fetus and also changes as labor progresses. In addition, the amount of meconium excreted prior to birth varies significantly from fetus to fetus. Thus there are two variables, the amount of amniotic fluid and the amount of meconium excreted, which determine the concentration of meconium in the amniotic fluid. It is also known that the aspiration of amniotic fluid with a high concentration of meconium is a life threatening problem for newborn infants. The present invention provides a direct and inexpensive method for measuring the concentration of meconium in amniotic fluid.

Referring to FIG. 1, there is shown a first preferred embodiment of a meconium measurement chart 100 for use in evaluating the meconium content of amniotic fluid. The chart 100 is a transparent plastic or glass plate 102 with several color samples 104A-104E imprinted or embedded in the plate. Each color sample 104 matches the color and transparency of amniotic fluid having different amounts of meconium therein. In particular, the chart is arranged so that the color samples 104A-104E correspond to increasing amounts of meconium content. In the preferred embodiment, there are numerical indicia 106A-106E next to the color samples for denoting meconium content measurement values. The indicia do not follow any particular measurement system, but instead are used only to indicate the relative amount of meconium in an amniotic fluid sample.

In some embodiments, the chart includes a marker 108 which forms a dividing line between those colors which indicate an acceptable level of meconium content and those colors which indicate that a dangerous level meconium is present in an amniotic sample. In the chart 100 shown in FIG. 1, amniotic fluid samples which most closely match color samples 1 and 2 (104A and 104B) do not have significant meconium content and do not require precautionary measures. Those amniotic fluid samples which match color samples 3 through 5 (104C through 104E) indicate that the fetus has discharged a sufficient amount of meconium into the mother's amniotic sac prior to birth that precautionary measures are called for.

When the chart 100 is vertically oriented, measurements above the line 108 indicate that it is unlikely that there is significant meconium content in the amniotic fluid, while measurements below the line indicate that there is significant meconium content in the amniotic fluid.

Note that since the only relevant question is whether the amniotic fluid is darker or lighter than the threshold level corresponding to marker 108, it is possible to use a chart having only a marker 108, with no other concentration indicators 104. More generally, the chart 100 will generally have at least one concentration indicator so that the meconium content of a sample can be evaluated relative to the color at that indicia.

The number of color samples 104 used in a meconium measurement color chart 100 will typically vary between four and eight. In a first preferred embodiment, the number of color samples is five. Since the Figures herein do not show color, the colors will be described herein qualitatively and quantitatively. Meconium is a very dark brown substance which borders on being black. The primary color components of meconium are thus yellow and green. Color sample 104A is a pale gray; color sample 104B is a pale yellow; color sample 104C is a dirty yellow or khaki color which looks slightly brown; color sample 104D is tan or light brown, and color sample 104E is green/brown. Quantitatively, the five color samples 104A-104E are characterized by the following table of color definitions, which are based on the industry standard color tables used by printers and graphic artists, and meconium concentrations.

TABLE 1

| COLOR CHART DEFINITIONS | |
|---|---|
| SAMPLE COLOR | MECONIUM DILUTION |
| SAMPLE 1 Cool Gray 1 | Pure Amniotic Fluid |
| SAMPLE 2 Pantone 133-U | 1:128 |
| SAMPLE 3 Pantone 457-U | 1:32 |
| SAMPLE 4 Pantone 458-U | 1:12 |
| SAMPLE 5 Pantone 460-U | 1:4 |

The first color sample 104A corresponds to pure amniotic fluid without any meconium, the second color sample 104B corresponds to a concentration of one part meconium to 128 parts amniotic fluid, and the other three samples correspond to increasing concentrations of meconium in amniotic fluid. There is some variation in the consistency of meconium to from fetuses to fetuses, but these variations are not significant. Thus the amount of fecal material in a 3% solution of meconium will vary somewhat from infant to infant. As a result, the color scale used in the preferred embodiment of the present invention is based on the average colors of meconium solutions made using meconium samples taken from a number of infants.

Referring to FIG. 2, a second preferred embodiment of a meconium measurement chart 130 has a color strip 132 which contains a continuous color spectrum, somewhat like a rainbow, except that the colors vary from a very pale gray at the top end to a dark green-brown (corresponding to Pantone 460-U) at the other end. The yellow component of the color spectrum increases linearly from one end of the strip 132 to the other, and the green component of the color spectrum starts with a value of zero around forty percent of the way down the strip and increases linearly from there to the bottom end of the strip 132. A set of indicia 136A-136E are located alongside the color strip 132 for denoting a meconium content measurement. As with the chart 100 shown in FIG. 1, these indicia do not follow any particular measurement system, but instead are used only to indicate the relative amount of meconium in an amniotic fluid sample.

The spectral components at each of these five indicia 136A-136E are the same as those listed in Table 1 for the color chart 100 in FIG. 1.

In some embodiments, the chart 130 includes a line or other marker 138 which forms a dividing line between those colors which indicate an acceptable level of meconium content and those colors which indicate that a dangerous level meconium is present in an amniotic sample. When the chart 130 is vertically oriented, measurements above the line 138 indicate that it is unlikely that there is significant meconium content in the amniotic fluid, while measurements below the line 138 indicate that there is significant meconium content in the amniotic fluid.

In particular, any meconium measurement higher than "2" (i.e., which is darker than Pantone 133-U) indicates that there is significant meconium content in the amniotic fluid and that precautionary measures should be taken to intubate the infant so as to prevent or minimize the infant's aspiration of meconium.

Referring to FIGS. 3 and 4, the meconium measurement color chart 100 or 130 is used as follows. Typically, a sample of amniotic fluid is obtained from a patient either after the patient's amniotic sac breaks during labor, or by means of a syringe. In either case, a sample of amniotic fluid 150 is placed in or on a transparent holder 152, such as a slide or a test tube (step 160). Then both the amniotic fluid sample and the meconium measurement chart 100 are held in front of a fluorescent light panel 154, similar to the light panels used to view X-rays, so that the fluorescent light shines through both the sample 150 and the chart 100 (step 162). The user then visually compares the two to determine either (1) which color sample 104 in the chart 100 most closely matches the color of the amniotic fluid sample 150, or (2) whether the meconium content measurement falls above or below the threshold marker 108. In either case, the user compares and evaluates the meconium content of an amniotic fluid sample (step 164).

In the preferred embodiment, the fluorescent light uses a blue fluorescent bulb, such as the blue fluorescent bulbs used in x-ray light panels. In other embodiments it would also be possible to use a pink fluorescent bulb, but one should not use yellow fluorescent bulbs because yellow is an important color component of meconium.

Referring to FIG. 5, in another embodiment of the present invention the measurement chart 100 or 130 is combined with the fluid sample holder 152. In particular, this embodiment uses an amniotic fluid container 180 with a meconium measurement chart 182 imprinted thereon for evaluating the meconium content of an amniotic fluid sample. The "container" 180 may be a test tube, any other type of fluid container, or even a laboratory slide.

It is noted that fetuses often excrete meconium during labor. Meconium excreted late in the labor may be as dangerous to the fetus as meconium excreted at an earlier time. Therefore it is anticipated that the present invention may be used more than once during labor to monitor the concentration of meconium in the amniotic fluid and to detect those instances when the infant excretes meconium during labor.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A method of evaluating meconium content of an amniotic fluid sample, the steps of the method comprising:

placing a sample of amniotic fluid in a transparent medium;

providing a color chart depicting fluid colors which correspond to various levels of meconium content in amniotic fluid, said color chart including at least one meconium concentration indicia corresponding to a predefined color in said color chart; and comparing said amniotic fluid sample with said color chart and determining the meconium concentration level of said amniotic fluid sample relative to said meconium concentration indicia.

2. The method of evaluating meconium content of an amniotic fluid sample as set forth in claim 1, further including the step of shining white fluorescent light through said amniotic fluid sample and said color chart;

said comparing step including the step of visually comparing the color of said amniotic fluid sample with the colors in said color chart.

3. A method of evaluating meconium content of an amniotic fluid sample, the steps of the method comprising:

obtaining a sample of amniotic fluid;

providing a color chart depicting a multiplicity of distinct colors which correspond to various levels of meconium content in amniotic fluid, said color chart including at least one meconium concentration indicia corresponding to a predefined color in said color chart; and comparing said amniotic fluid sample with said color chart and determining the meconium concentration level of said amniotic fluid sample relative to said meconium concentration indicia.

4. The method of evaluating meconium content of an amniotic fluid sample as set forth in claim 3, said providing step including the step of providing a color chart having a multiplicity of distinct color samples which correspond to various levels of meconium content in amniotic fluid, said color chart including meconium concentration indicia corresponding to each of said color samples;

said comparing step including the step of visually comparing the color of said amniotic fluid sample with the colors samples in said color chart and selecting the meconium concentration indicia for a color sample in said color chart which most closely matches the color of said amniotic fluid sample.

5. The method of evaluating meconium content of an amniotic fluid sample as set forth in claim 3, said providing step including the step of providing a color chart depicting a continuous color spectrum having colors which vary from a pale yellow color at one end of said spectrum to a green-brown color at another end of said spectrum, said color chart having at least one meconium content indicia neighboring a corresponding predefined color in said color spectrum.

6. The method of evaluating meconium content of an amniotic fluid sample as set forth in claim 3, further including the step of shining fluorescent light through said amniotic fluid sample and said color chart;

said comparing step including the step of visually comparing the color of said amniotic fluid sample with the colors in said color chart.

* * * * *